United States Patent [19]

Shaobo

[11] Patent Number: 5,783,562
[45] Date of Patent: Jul. 21, 1998

[54] LUTEINIZING HORMONE RELEASING HORMONE ANALOGS

[75] Inventor: Xiao Shaobo, Tianjin, China

[73] Assignee: Asta Medica Aktiengesellschaft, Germany

[21] Appl. No.: 450,951

[22] Filed: May 23, 1995

Related U.S. Application Data

[63] Continuation-in-part of Ser. No. 265,631, Jun. 24, 1994, abandoned, which is a continuation of Ser. No. 789,730, Nov. 12, 1991, abandoned.

[30] Foreign Application Priority Data

Nov. 10, 1990 [CN] China .................... 90108955.9

[51] Int. Cl.$^6$ .................... A61K 38/00; A61K 38/24; A01N 37/18; C04K 5/00
[52] U.S. Cl. .................... 514/15; 514/2; 514/800; 530/313; 530/328; 938/110
[58] Field of Search .................... 514/2, 15, 800; 530/313, 328; 938/110

[56] References Cited

U.S. PATENT DOCUMENTS

| | | | |
|---|---|---|---|
| 4,642,332 | 2/1987 | Folkers et al. | 570/313 |
| 4,652,550 | 3/1987 | Rivier et al. | 630/313 |
| 4,690,916 | 9/1987 | Nestor, Jr. et al. | 530/313 |
| 4,801,577 | 1/1989 | Nestor, Jr. et al. | 530/313 |
| 4,851,385 | 7/1989 | Roeske | 530/313 |
| 5,140,009 | 8/1992 | Haviv et al. | 530/313 |
| 5,296,468 | 3/1994 | Hoeger et al. | 530/313 |
| 5,300,492 | 4/1994 | Haviv et al. | 530/313 |

FOREIGN PATENT DOCUMENTS

| | | |
|---|---|---|
| 0277829 | 2/1988 | European Pat. Off. |

OTHER PUBLICATIONS

Karl Folkers, et al., Increased Potency of Antagonists of the Luteinizing Releasing Hormone Which Have D-3-PAL in Position 6. Biochemical and Biophysical Research Communications, Jun. 13, 1986, vol. 137, No. 2, pp. 709–715.

Karl Folkers, et al., Activities of Antagonists of the Luteinizing Hormone Releasing Hormone with Emphasis on Positions 1, 5 and 6 and on Positions 1, 2 and 3. Z. Naturforsch. 42b, 101–106 (1987); received Jul. 18, 1986.

Karl Kolers, et al., Relative Potencies of Antagonists of the Luteinizing Hormone Releasing Hormone with Lys$^8$ and Arq$^8$ and Substitutions in Positions 3, 5, 6, 7, and 8. pp. 1087–1091; received Jun. 10, 1986.

Kelliang Liu, et al., Antagonists of Luteinizing Hormone Releasing Hormone with Novel with Unnatural Amino Acids at Position Six. Int. J. Peptide Protein Res. 35, 1990, 157–160.

Karten et al, Endocrine Reviews, vol. 7(1), pp. 44–66, (1986).

Karl Folkers, et al., Increased Potency of Antagonists of the Luteinizing Hormone Releasing Hormone Which Have D-3-PAL in Position 6. Biochemical and Biophysical Research Communications, Jun. 13, 1986, vol. 137, No. 2, pp. 709–715.

R.W. Roeske et al., LHRH Antagonists with Low Histamine Releasing Activity, pp. 17–24.

Liu Ke-Liang et al., Synthesis and Bioactivities of New LHRH Antagonists Containing Novel Unnatural Amino Acids at Position File. vol. 34 No. 2 Received Jul. 3, 1989.

Marvin J. Karten et al., Gonadotropin–Releasing Hormone Analog Design. Structure–Function Studies toward the Development of Agonists and Antagonists: Rationale and Perspective. Vo. 7, No. 1.

Karl Folkers et al., Activities of Antagonists of the Luteinizing Hormone Releasing Hormone with Emphasis on Positions 1, 5 and 6 and on Positions 1, 2 and 3. Z. Naturforsch. 42b, 101–106 (1987); received Jul. 18, 1986.

Karl Folkers et al., Relative Potencies of Antagonists of the Luteinizing Hormone Releasing Hormone with Lys$^8$ and Arq$^8$ and Substitutions in Positions 3, 5, 6, 7 and 8. pp. 1087–1091 (1986); received Jun. 10, 1986.

Kelliang Liu et al., Antagonists of luteinizing hormone releasing hormone with novel unnatural amino acids at position six. Int. J. Peptide Protein Res. 35, 1990, 157–160.

*Primary Examiner*—Cecilia J. Tsang
*Assistant Examiner*—Jennifer Harle
*Attorney, Agent, or Firm*—Cushman Darby & Cushman IP Group of Pillsbury Madison & Sutro

[57] ABSTRACT

A method is provided for the design and synthesis of Leuteinizing Hormone Releasing Hormone (LHRH) antagonists having exact amino acid sequences and containing 5–100 amino acids. This method can be used to produce peptides useful in treating disorders of the reproductive endocrine system, including endometriosis, precocious puberty, prostate cancer and breast cancer. Additionally, peptides produced by this method can be used as contraceptives for either males or females. Peptides produced by this method can further be employed in the diagnosis and treatment of infertility.

8 Claims, 3 Drawing Sheets

LUTEINIZING HORMONE RELEASING HORMONE ANALOGS

This application is a Continuation-In-Part of Ser. No. 08/265,631, filed Jun. 24, 1994, now abandoned, which is a Continuation of Ser. No. 07/789,730, filed Nov. 12, 1991, now abandoned.

BACKGROUND OF THE INVENTION

This invention consists of two parts: 1) a method of design and synthesis of peptides, or their derivatives, which have exact amino acid sequences and contain 5–100 amino acid residues; and 2) products obtained by using the above method. Taking NAc-D2Nal$^1$-DpClPhe$^2$-D3Pal$^3$-Ser$^4$-Tyr$^5$-DArg$^6$-Leu$^7$-Arg$^8$-Pro$^9$-DAla$^{10}$-NH 2 as the parent-compound, a series of new analogs expressed as NAc-D2Nal$^1$ -AA$^2$-AA$^3$-Ser$^4$-AA$^5$-AA$^6$-Leu$^7$-AA$^8$-Pro$^9$ -DAla$^{10}$-NH$_2$ are obtained by fine modification of both the lipophilic region and the alkaline region of the parent compound. In this way, the high antiovulatory activity of the parent compound can be maintained, and the histamine releasing activity can be reduced to a level sufficient to meet clinical requirements. Acting as medicinal peptides, the compounds described herein can be used as contraceptives and for treating disorders related to reproductive endocrinology.

SUMMARY OF THE INVENTION

The present invention relates to novel peptides and derivatives thereof which have exact chemical structures.

The present invention is also directed to methods of preparing the above novel peptides and their derivatives and to applications thereof.

The present invention further provides new LHRH antagonists having very high antiovulatory activity (AOA), very low HRA and negligible side effects.

Hypothalamic luteinizing hormone releasing hormone (LHRH) is known to act upon the anterior pituitary gland to stimulate the secretion of luteinizing hormone (LH) and follicular stimulating hormone (FSH). In turn, antagonistic analogs of LHRH are useful in that they act rapidly upon the anterior pituitary, they are viable for long periods of time and they can be safely and reversibly used for contraception and/or selective suppression of gonadotropin secretion. LHRH antagonists have been found to be superior to agonists as contraceptives and for use in suppressing gonadotropin secretion. Among the more than two thousand LHRH analogs which have been designed and synthesized, the "Nal-Arg" analog has shown fairly high antifertility activity. However, the "Nal-Arg" analog has also shown a very strong histamine-releasing activity (HRA). Moreover, the "Nal-Arg" analog causes transient edema of the face and extremities in rats when administrated at dosages as high as 50–100 times that of therapeutic dosages. These histamine-related systemic effects were affirmatively demonstrated in a clinical trial. Other LHRH antagonists containing DArg$^6$ or DLys$^6$ have shown similar histamine-related side effects, with the ED$_{50}$ (effective dose for 50% response) values for HRA falling below 1 μg/ml.

The design methodology of this invention is based upon the topological similarity between the molecule of a parent compound NAc-D2Nal$^1$-DpClPhe$^2$-D3Pal$^3$-Ser$^4$-Tyr$^{55}$-DArg$^6$-Leu$^7$-Arg$^8$-Pro$^9$-DAla$^{10}$-NH$_2$ (II) and a neuropeptide, Substance P (SP). The parent compound is modified in both the alkaline and the lipophilic regions of the parent compound, resulting in new antagonists having both a high AOA and a low HRA. The term "modified," as used herein, refers to adjustments or substitutions of amide acids in the Tyr$^5$-DArg$^6$-Arg$^8$ region of the C-terminus and the aromatic acids in N-terminus of compound (II). More specifically, the design involves the introduction of a suitable alkaline group and the substitution of unnatural amino acids at positions 2, 3, 5, 6 and 8 of compound (II).

The following represent additional methods and examples of the claimed invention.

Substitution of D3Pal$^3$ (an aromatic amino acid having suitable basicity) for DArg$^6$ in compound (II) in order to obtain analog (III): NAc-D2Nal$^1$-DpClPhe$^2$-D3Pal$^3$-Ser$^4$-Tyr$^5$-D3Pal$^6$-Leu$^7$-Arg$^8$-Pro$^9$-DAla$^{10}$-NH$_2$.

Substitution of Arg$^5$ for Tyr$^5$ in compound (III) in order to obtain compound (IV): NAc-D2Nal$^1$-DpClPhe$^2$-D3Pal$^3$-Ser$^4$-Arg$^5$-D3Pal$^6$-Leu$^7$-Arg$^8$-Pro$^9$-DAla$^{10}$-NH$_2$.

Substitution of DPhe$^3$, or its DXCH$_2$Phe derivatives, for D3Pal$^3$ in compound (IV) in order to obtain compound (V): NAc-D2Nal$^1$-DpClPhe$^2$-DPhe$^3$ Ser$^4$-Arg$^5$-D3Pal$^6$-Leu$^7$-Arg$^8$-Pro$^9$-DAla$^{10}$-NH$_2$, or its DXCH$_2$Phe$^3$ analogs.

Substitution of DPhe$^3$, or its derivatives, for D3Pal$^3$ in compound (III) in order to obtain compound (V): NAc-D2Nal$^1$-DpClPhe$^2$-DPhe$^3$- Ser$^4$-Tyr$^5$-D3Pal$^6$-Leu$^7$-Arg$^8$-Pro$^9$-DAla$^{10}$-NH$_2$, or its DXCH$_2$Phe$^3$ analogs.

According to the present invention, a new series of LHRH antagonists having the formula NAc-D2Nal$^1$-AA$^2$-AA$^3$-Ser$^4$-AA$^5$-AA$^6$-Leu$^7$-AA$^8$-Pro$^9$-DAla$^{10}$-NH$_2$ have been synthesized, wherein AA represents either natural or unnatural amino acids which are expressed as either D- or L-YAla. More specifically:

AA$^2$=D-pClPhe, D-YAla, DPhe, Y-Ala, DXCH$_2$Phe;

AA$^3$=D3Pal, Y-Ala, D-Yala, DPhe, D-XCH$_2$Phe;

AA$^5$=Arg, DMap, Pip, Tyr, Pal, Mop, Tep, Map, Phe, Eap, Pap, Bap, DMop;

AA$^6$=D3Pal, D-YAla, D-XCH$_2$Phe;

AA$^8$=Pip, Mop, Tep, Map, Eap, Pap, Bap, Arg;

in which Y =H or Ar,

Ar=wherein

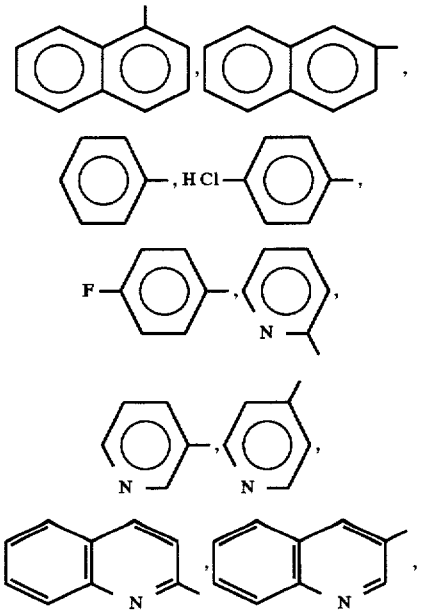

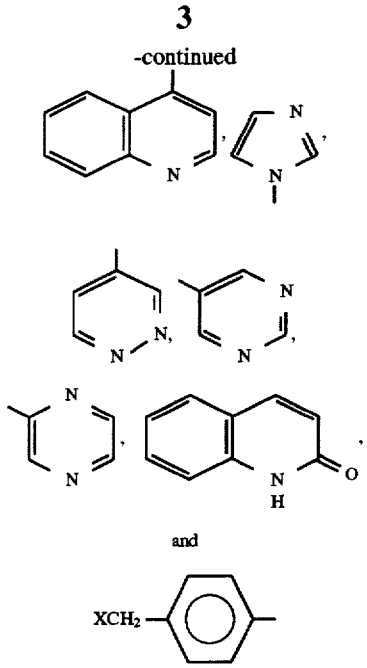

and

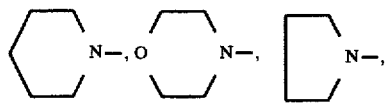

in which
X=

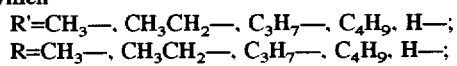

in which
R'=CH$_3$—, CH$_3$CH$_2$—, C$_3$H$_7$—, C$_4$H$_9$, H—;
R=CH$_3$—, CH$_3$CH$_2$—, C$_3$H$_7$—, C$_4$H$_9$, H—;

The LHRH antagonists obtained by using the above described method can be used to treat disorders of the reproductive endocrine system, including endometriosis, precocious puberty, prostate cancer and breast cancer. Additionally, these LHRH antagonists can be used as contraceptives for both males and females, and may further be employed in the diagnosis and treatment of infertility. The LHRH antagonists of the present invention can be prepared as normal injections, injectable capsules or other formulations for real application.

In the natural course of histamine release in the body, neuropeptide SP has been found to play a very important role. The ED$_{50}$, of neuropeptide SP for HRA is 5–15 μM. The chemical structure of neuropeptide SP is Arg$^1$-Pro$^2$-Lys$^3$-Pro$^4$-Gln$^5$-Gln$^6$-Phe$^7$-Phe$^8$-Gly$^9$-Leu$^{10}$-Met$^{11}$-NH$_2$. A study of the relationship between the structure of neuropeptide SP and HRA showed that Arg$^1$-Pro$^2$-Lys$^3$ in the N-terminus is essential to neuropeptide SP's HRA, since deletion of these three amino acids from the neuropeptide SP molecule were discovered to entirely abolish neuropeptide SP's HRA. By contrast, when one, two or three amino acids were deleted from the C-terminus of the neuropeptide SP molecule, the HRA remained as high as one fourth the HRA of the unaltered neuropeptide SP molecule. With the further deletion of Phe$^8$ and Phe$^7$, the HRA was reduced to 4% and 0.57% of unaltered neuropeptide SP. Deletion of Gln$^{5,6}$ did not cause a significant change in the HRA. The above data demonstrates, therefore, that the lipophilic region around Phe$^{7,8}$ determines the HRA value, and that this region is involved in the binding of the neuropeptide SP molecule to the mast cell receptor.

As previously mentioned, the D2Nal$^1$, DArg$^6$ analogs of LHRH showed a very high HRA, and their molecular structures possessed similar topology to neuropeptide SP. The DArg$^6$-Leu$^7$-Arg$^8$ sequence found in the D2NAl$^2$, DArg$^6$ analogs of LHRH appear to correspond to the Arg$^1$-Pro$^2$-Lys$^3$ sequence in the neuropeptide SP molecule. These corresponding regions each consist of a pair of strongly basic amino acid residues between which only one neutral amino acid residue is present, i.e., both the D2Nal$^1$, DArg$^6$ analogs of LHRH and the neuropeptide SP molecule each contain two strongly basic amino acid residues at positions 1 and 3. On the other hand, a cluster of aromatic amino acid residues in the D2Nal$^1$, DArg$^6$ analogs of LHRH is considered to correspond to the Phe$^{7,8}$ region of the neuropeptide SP molecule in determining the magnitude of the HRA.

DETAILED DESCRIPTION OF THE INVENTION

Figure 1:
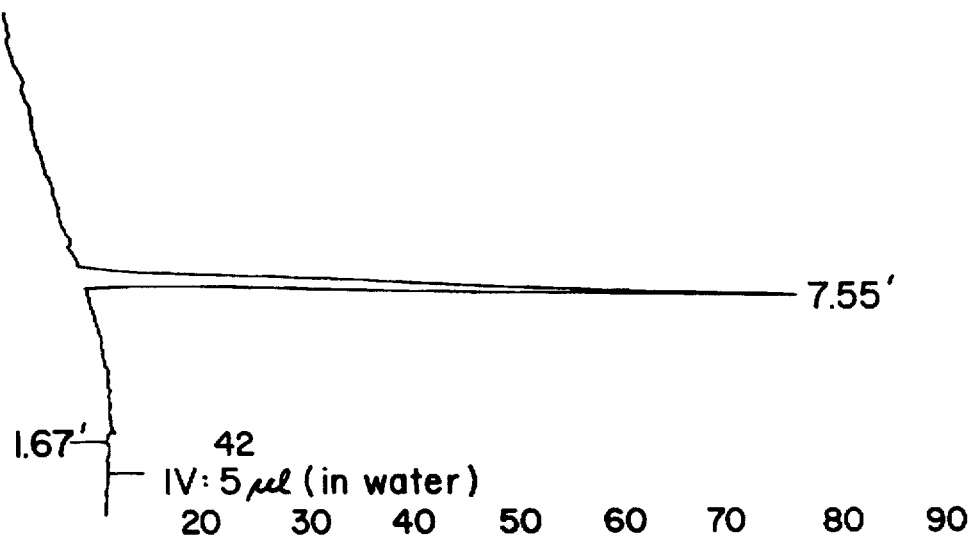
FIG. 1 shows the reverse-phase high performance liquid chromatography (HPLC) spectra for a pure sample of LHRH antagonist (IV).
Conditions:
Column: μ-Bondapek C18 (3.9 mm×30 cm)
Moble Phase: A, 0.1 M NH$_4$OAC (pH 7) B, 20% A+80% acetonitrile
Gradient Procedure: B from 10% to 100% in 15min.
Flow Rate: 2 ml/min.
Detector: UV 229 nm.

The design of the present invention consists of two parts: (1) modifying the Tyr$^5$-DArg$^6$-Arg$^8$ region of the C-terminus, and (2) fine adjusting the aromatic acids after optimizing the modification of the alkaline region of C-terminus. Using NAc-D2Nal$^1$-DpClPhe$^2$-D3Pal$^3$-Ser$^4$-Tyr$^5$-DArg$^6$-Leu$^7$-Arg$^8$-Pro$^9$-DAla$^{10}$-NH$_2$ (II) as the parent compound, the AOA was shown to be 100% at 0.5 μg in corn oil and 57% at 0.25 μg.

In modifying the Tyr$^5$-DArg$^6$-Arg$^8$, DArg$^6$ in compound (II) can be replaced by weakly basic or neutral aromatic acids, such as D3Pal, D6Qal, tetrahydro tryptophan and methyl tryptophan. When D3Pal⁶ was substituted for DArg⁶ in compound (II), the compound NAc-DNal¹-DpClPhe²-D3Pal³,⁶, DAla¹⁰ (III) was obtained. Compound (III) showed an AOA of 100% at 3 µg, 83% at 1 µg (in corn oil), and an $ED_{50}$ of 9.8 µg/ml for HRA, which was much better than that of the "Nal-Arg" analog ($ED_{50}$ for HRA was less than 1 µg/ml). In order to obtain a high AOA, it appears that the basicity of the whole molecule should equal to or similar to that of a pair of arginines. Because position 5, like position 6, is not involved with receptor binding, a wide variety of amino acids, including arginine, can be inserted at position 5.

In the present invention, a series of new analogs were designed. For example, substitution of Arg⁵ for Tyr⁵ in compound (III) resulted in NAc-DNal¹-DpClPhe²-D3Pal³,⁶, Arg⁵, DAla¹⁰ (IV). Compounds (II) and (IV) both contained two arginines, although the distance between the two arginines in compound (IV) was larger than that found in compound (II). This is explained by the fact that the geometric relationship between the two arginines in compounds (IV) became 5 and 8 (i.e., two other amino acids were positioned between the two arginines). For this reason, the HRA of compound (IV) would be reduced, and because of the presence of the two arginines, the AOA of compound (IV) should not be lower than that of compound (II). The bioassay results for compound (IV) showed that the $ED_{50}$ for HRA was 3.5 µg/ml, while the AOA for compound (IV) was 50% at 0.125 µg (in corn oil), 85% at 0.25 µg and 100% at 0.5 µg.

The above results represented the first time that an LHRH antagonist achieved an $ED_{50}$ for AOA that was equal to or less than 0.125 µg. Based upon these results, further design was predicated upon the structure of compound (IV).

There are four alkaline residues, D3Pal³,⁶ and Arg⁵,⁸, found in compound (IV), whereas compound (II) contains only three alkaline residues. Therefore, it was reasonable to replace one D3Pal with a neutral amino acid. Compound (IV) showed very strong hydrophilicity, and reducing the hydrophilicity of compound (IV) by substituting a hydrophobic amino acid for D3Pal would enhance retention of the drug in the body, thereby extending its effective duration.

A new series of analogs were then designed by substituting various hydrophobic amino acids for D3Pal³ in compound (IV). The most efficacious analog produced was Nac-D2Nal¹-DpClPhe²-DPhe³-Arg⁵-D3Pal⁶, DAla¹⁰ (V), in which DPhe³ was substituted for D3Pal³. Compound (V) showed 100% of the AOA at 1 µg (in saline), which was equal to that of parent compound (IV), while the HRA was reduced by one-half (the $ED_{50}$ for HRA was 7.4 µg/ml).

Further substitution of DPhe² for DpClPhe² reduced the lipophilicity of this region of the molecule and correspondingly reduced the HRA.

The Arg⁵-D3Pal⁶-Leu⁷-Arg⁸ portion of the C-terminus of compound (IV) seems to play a major role in triggering histamine release. The D3Pal residue combines aromaticity, basicity and hydrophilicity in one molecule, and it is steroacceptable in LHRH antagonists for receptor binding. Similarly, the design of a new series of unnatural amino acids possessing the same characteristics as D3Pal may lead to even better LHRH antagonists than those of compounds (IV) and (V).

Modification of natural, lipophilic and aromatic amino acids (e.g., phenylalanine)—as demonstrated, for example, by the method described below under the heading "The Synthesis of Novel Unnatural Amino Acids"—leads to a series of novel amino acids that combine aromaticity, hydrophilicity and basicity into one molecule, which can expressed by the formula:

$$R_1R_2NCH_2C_6H_4CH_2CH(NH)CO_2H \qquad (VI),$$

where $R_1$ and $R_2$ may be the same or different from each other, they may be chain-like or cyclic, and they may contain a hetero-atom. With changes in the $R_1$ and $R_2$ positions, a series of amino acids can be obtained which show systematically changed basicity, hydrophilicity and configuration. Introduction of those amino acids into position 5, 6 and 8 of compound (IV) have given a series of three new antagonists of LHRH. Bioassay results showed that each series gave at least one new antagonist showing 100% AOA at 1 µg, which is similar to that of compound (IV), whereas the HRA was significantly reduced.

An example of a new antagonist was compound (VII), which has the following formula:

$$NAc\text{-}D2Nal^1\text{-}DpClPhe^2\text{-}D3Pal^3\text{-}Ser^4\text{-}Mop^5\text{-}D3Pal^6\text{-}Leu^7\text{-}Arg^8\text{-}Pro^9\text{-}DAla^{10}\text{-}Nh_2.$$

Compound (VII) showed 100% AOA at 1 µg and had an $ED_{50}$ of 14.7 µg/ml for HRA, which appeared to be better than compound (V). When substitution of compound (VI) for Arg⁸ in compound (IV) was made, it was determined that the extent of HRA decrease was positively correlated with the length of R in compound (VI). Therefore, the $ED_{50}$ for HRA could be made higher than 200 µg/ml, such that the resulting compounds could be easily dissolved in aqueous solution and utilized clinically without formulation problems. The results demonstrated that Arg⁵ and Lys⁸ are not essential for highly potent LHRH antagonists. A suitable alkaline center at position 8 will ensure a high AOA, with activity inducing mast cells to release histamine being remarkably reduced when the basic center possesses chemical modification.

This invention combines modifications at both the N-terminus and C-terminus that lead to better LHRH antagonists.

The process of synthesis is illustrated as follows:

1. The Synthesis of Novel Unnatural Amino Acids

Over 60 series and nonseries, D- or L-amino acids are designed and synthesized through the four synthetic routes outlined in the scheme below. The structures of these unnatural amino acids are shown with the general structural formulas listed in the same scheme. Some of these amino acids have alkalinity, hydrophilicity and aromaticity respectively, while others possess all three characteristics in the same molecule.

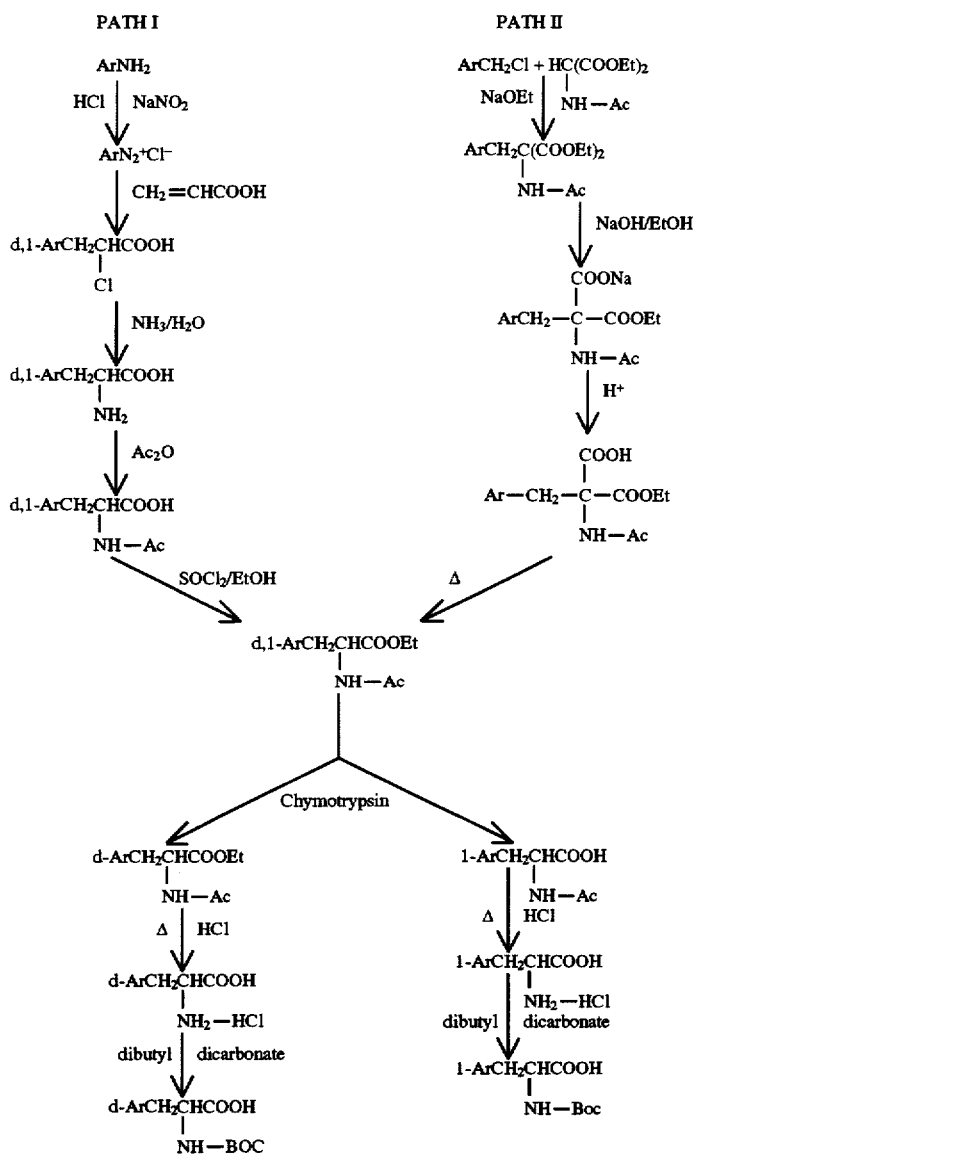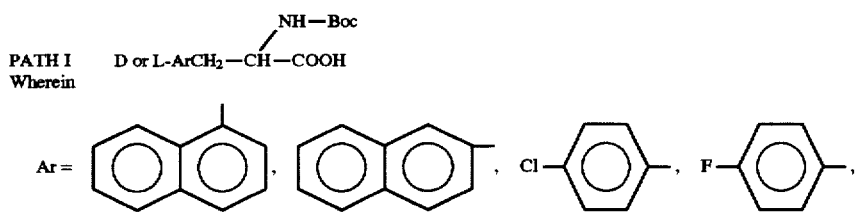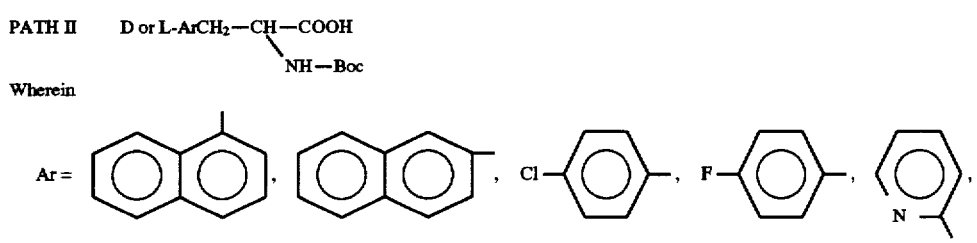

-continued
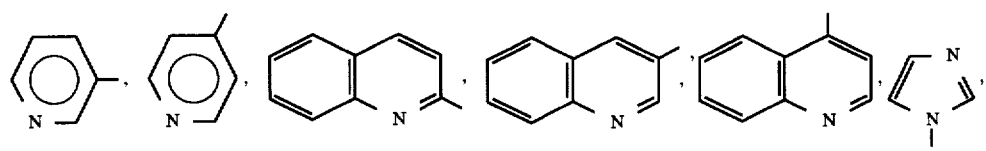
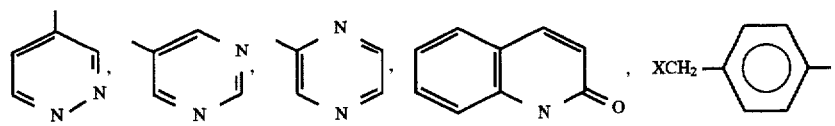
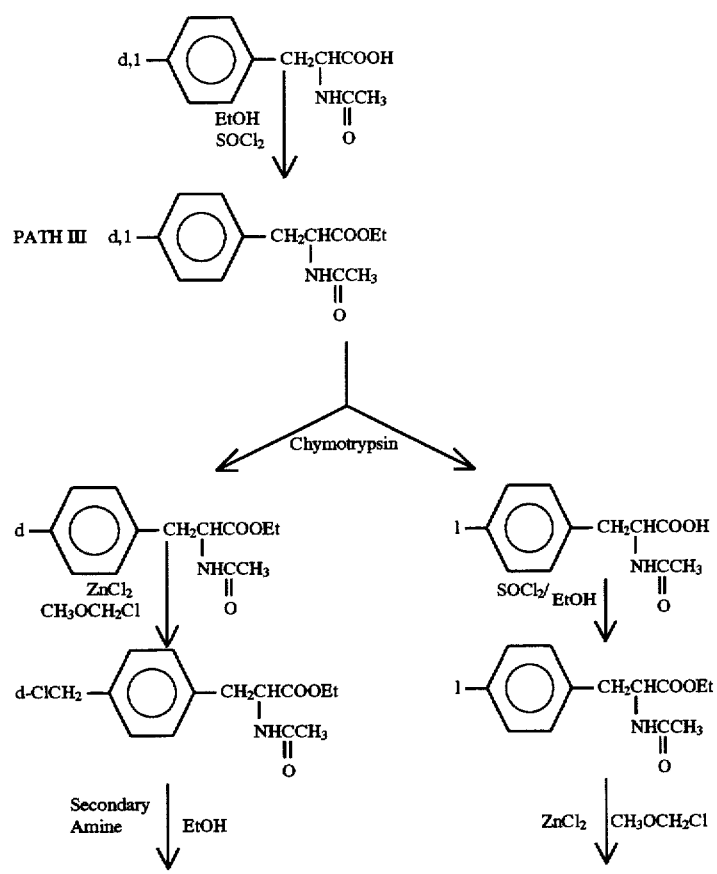

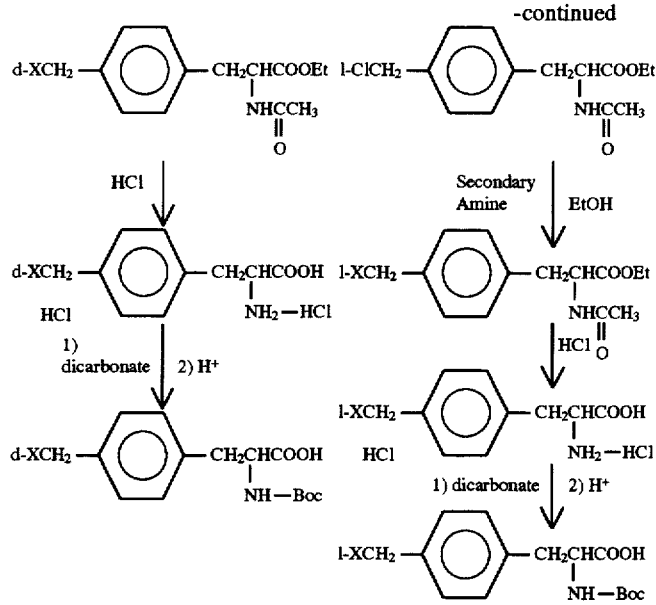
PATH III   D or L-XCH₂—⟨benzene⟩—CH₂CHCOOH   Wherein
                                    |
                                    NH—Boc
X = piperidin-N—, morpholin-O N—, pyrrolidin-N—, R'₂N—, RR'N—
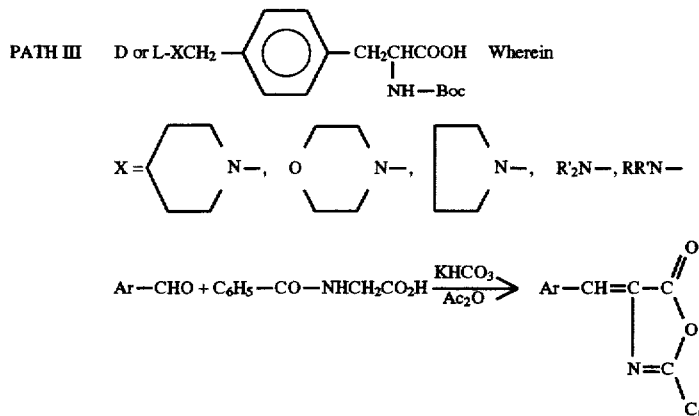
PATH IV
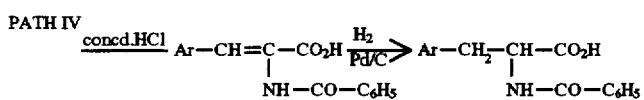
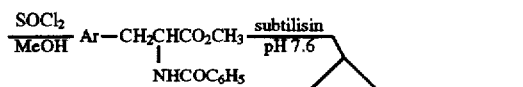
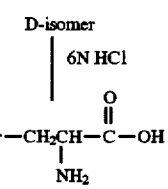     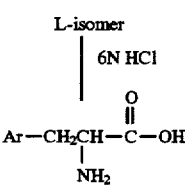
(D-amino acid)        (L-amino acid)
PATH IV   D or L   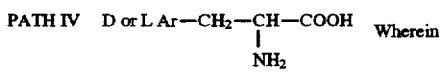   Wherein

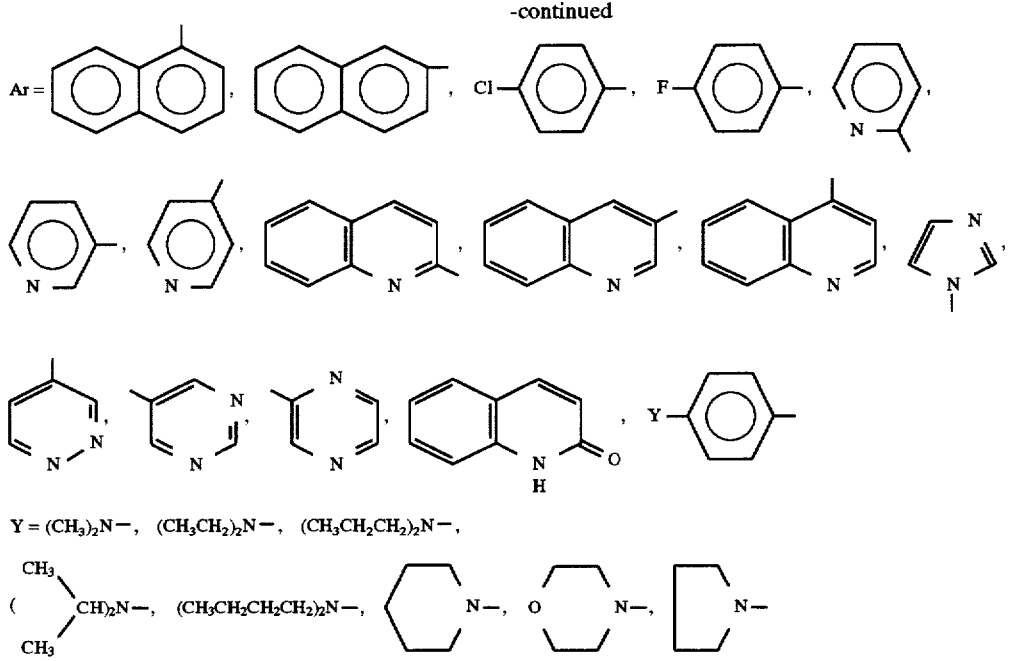

Y = (CH₃)₂N—, (CH₃CH₂)₂N—, (CH₃CH₂CH₂)₂N—,

2. Synthesis of Peptide

Synthesis of the peptides begins from the C-terminus of the peptide on benzhydrylamine hydrochloride resin (BHA resin) utilizing the method of solid-phase peptide synthesis introduced by Merrifield. It is a three-step process including anchor, coupling and cleavage. Dichloromethane (DCM) is the major solvent used for washing between each step of the reaction, while isopropanol alcohol (IPA) and N, N-dimethylformamide (DMF) are also used when necessary. The coupling reaction, catalyzed by excessive dicyclohexylcarbodiimide (DCC), is carried out with a sufficient amount of 1-hydroxybenzotriazole (HOBT). The degree of the coupling reaction is monitored with Kaises ninhydrin method. A second coupling reaction is to be carried out if the Kaises test gives a positive result. The peptide chain is cleaved from the resin using anhydrous hydrogen fluoride (HF) in the presence of anisole once all necessary reactions on the resin have been completed. At the same time the peptide chain is cleaved, the temporary protecting group becomes unprotected. After washing with ethyl acetate or ether, crude products of LHRH antagonists are obtained by means of aqueous acetic acid extraction, which is then followed by lyophilization. The yield has been shown to be over 50%.

3. Purification of Peptide (1) The peptide is purified by gel permeation chromatography or silica partition chromatography through a column as high as 60–100 cm with the aid of UV/TLC monitoring. The once purified antagonists are obtained after lyophilizing the major fractions. The yield is 50–90%, and the purity can be over 90%.

(2) The peptide is then further purified on a Waters high performance liquid chromatography (HPLC) instrument using a reverse phase C18 column (7.8×300 mm) (μ-Bondapak 84176). The yield of this step is 20–50%, while the purity is no less than 99%.

4. Purity Analysis of Peptide (1) TLC Analysis

The analysis is carried out on a plastic sheet coated by silica gel 60 F254 of 5–10 cm height. All of the sheets showed a single spot when developed in five different solvent systems.

(2) HPLC analysis

All of the peptides showed a single peak when eluted with two different solvent systems, which utilized a Waters HPLC instrument on a analytic column (μ-Bondapak 27324) when monitored by UV 210. The sample sizes were 10–200 μg.

5. Amino Acid Analysis of Peptide

According to the PICO-TAG method developed by the Waters Company, 50 μg of sample, which has been dried under vacuum for over 2 hours, is weighed accurately on a $10^{-5}$ g scale balance. After dissolving in water, a 10 μg aliquot is added to a reaction tube into which hydrochloride acid (1:1 ratio and containing 1% phenol) was added according to the Waters manual.

The reaction lasts 22–24 hours at 105° C. in a sealed container which has been filled with nitrogen and pumped to create a vacuum so that oxygen can be removed from the reaction tube. Phenol isothiocyanate is added to derive the amino group after evaporating off excessive hydrochloride acid. Then the reaction mixture was analyzed using an HPLC instrument equipped with a PICO-TAG amino acid analytical column and monitored by UV254. The content of each amino acid and relative mole ratios were calculated to give the amino acid composition of the sample based upon a comparison of the integrated area of each amino acid to that of an H-standard sample of Waters. The classic ion-exchange-ninhydrin derivation method (IEN) was also used as a control, which gave the same results. However, the IEN needed ten times more sample in order to provide a satisfactory result.

6. Evaluation of Biological Activity

Corbin's rat antiovulation method was used in the present invention. Healthy, adult, female SD rats (BW 200–250 g) were used in this experiment. All animals were maintained at 22°–24° C. and on a 14 hr./10 hr. (light/dark) schedule. They were given standard food and water ad libitum. Only those rats showing at least two consecutive 4-day estrous cycles in vaginal smear examination could be used in this experiment. The rats were given peptides (LHRH antagonists) at noon of proestrus with different doses in saline solution. The rats were sacrificed the next day, and both portions of their oviducts were examined using a dissecting microscope in order to determine the ovum number. The rats were divided into several groups according to the dosing, and each group consisted of about 10 rats. The control group, which was given an equivalent amount of saline, consisted of 9–10 rats. The antiovulatory activity (AOA) is shown in the following equation:

$$AOA = \frac{\text{Number of unovulated rats}}{\text{Total number of treated rats}} \times 100\%$$

7. Evaluation of Histamine Releasing Activity (1) Histamine releasing test (HRT) conducted in vitro:

The healthy, adult, male SD rats (BW 200–250 g) used in this experiment were housed in the same conditions as for the adult, female SD rats above. After anesthetizing with $CO_2$, the peritoneal cavity was washed with 50 ml of PIPES AC medium containing 20 units of heparin. Following centrifugation at 200×g for 8 min. at 4° C., the cells were washed again and resuspended to a concentration of 8-to-24×$10^5$ total leukocytes/ml in PIPAS AC. This suspension contained approximately 5–10% mast cells. Washed cells were used immediately after collection and were prewarmed for 5 min. at 37° C. prior to pipetting 0.3 ml aliquots into polystyrene tubes containing 0.3 ml of diluted peptide. The mixtures were incubated for 15 min. at 37° C., and the reaction was stopped by centrifugation at 400×g for 15 min. at 4° C. The supernatants were assayed for histamine content by manual fluorometric assay method after successful extraction with n-butanol and n-heptane. The histamine content can be obtained from the histamine standard curve (see below). The percentage of histamine release can be calculated from the following equation:

$$\text{Histamine release (\%)} = \frac{E-B}{C-B} \times 100\%$$

where E is the fluorometric reading of the experimental sample, B is the fluorometric reading of samples with cells and buffer only, and C is the fluorometric reading of "complete" samples (cells treated with $HClO_4$).

The standard curve can be obtained by plotting the OD values on a fluorometer at 350 nm/450 nm (activation/fluorescent) against the concentrations of serially diluted solutions of accurately weighed histamine hydrochloride. The relative parameter (r) of the histamine standard curve can be 0.9998, and the lowest detectable concentration of histamine is 0.5 ng/ml.

The $ED_{50}$ value of a peptide can be determined from the dose response curves obtained by plotting the histamine release versus the peptide concentration on semilogarithmic paper.

All peptide samples should be tested with mast cells from a minimum of 3 different rats.

(2) Cutaneous anaphylactoid activity test (CAT):

Healthy, adult, female SD rats (BW 250 g) were used in this experiment. The rats were injected intravenously with Evan's blue (1 ml of a 0.05% solution). Immediately after injection, 0.05 ml of peptide solution (5, 0.5 and 0.05 µg/ml respectively) and saline (control) were injected intradermally into a shaved section on the back of the animals. Then, 30 minutes after injection, the rats were sacrificed and the dorsal skin was measured. The diameters of the lesions were measured in millimeters in two perpendicular directions with a vernier caliper. Lesion diameters for the control rats were usually less than 5.5 mm.

The amount of Evan's blue permeating into the skin from the blood vessel can also be measured spectrophotometrically. The skin corresponding to the lesion area is cut down and immersed overnight in a mixture of acetone and saline (7:3 ratio). After centrifugation the following day, the content of Evan's blue in the supernatant is measured with a spectrophotometer (UV-260) at 610 nm against the reference solution of acetone and saline (7:3 ratio). Each peptide was tested in a minimum of 3 different rats.

A variety of new LHRH antagonists were designed and synthesized by means of the method described above. In brief, the new structure of LHRH antagonists was obtained by single or multiple substitution of the various natural and unnatural amino acids listed in the previous paragraphs.

Examples of the new LHRH antagonists obtained thereby are illustrated in Table 1.

TABLE 1

| | | | | Examples Related to This Invention | | | | | | |
|---|---|---|---|---|---|---|---|---|---|---|
| Analog | AA 1 | AA 2 | AA 3 | AA 4 | AA 5 | AA 6 | AA 7 | AA 8 | AA 9 | AA 10 |
| Parent | NAc-D2Na | DpClPhe | D3Pal | Ser | Tyr | DArg | Leu | Arg | Pro | DAla-NH2 |
| | | | | | Arg | | | | | |
| | | | | | Arg | DPhe | | Pip | | |
| | | | | | Arg | DMop | | Pip | | |
| | | | | | Arg | DPhe | | Mop | | |
| | | | | | Mop | D3Pal | | | | |
| | | | DPip | | Mop | DMop | | Pip | | |
| | | | | | Arg | D3Pal | | Pap | | |
| | | | | | Arg | D3Pal | | Pip | | |
| | | | | | DFPhe | D3Pal | | Pap | | |
| | | | | | | DPip | | Eap | | |
| | | | | | | DMap | | Mop | | |
| | | | DPhe | | Arg | DMop | | Map | | |
| | | | DpClPhe | | | DPip | | Map | | |
| | | | DPhe | | Arg | D3Pal | | | | |
| | | | | | Eap | | | Mop | | |
| | | | | | Tep | DMop | | Pep | | |
| | | | | | Tep | DMap | | Mop | | |
| | | | | | Tep | DEap | | | | |
| | | | | | Tep | DBap | | | | |
| | | | | | Tep | DPap | | | | |
| | | | | | Tep | DTep | | | | |

TABLE 1-continued

Examples Related to This Invention

| Analog | AA 1 | AA 2 | AA 3 | AA 4 | AA 5 | AA 6 | AA 7 | AA 8 | AA 9 | AA 10 |
|---|---|---|---|---|---|---|---|---|---|---|
| | | DpFPhe | D3Pal | | | DMop | | Mop | | |
| | | DPhe | | | Mop | DMop | | Eap | | |
| | | | | | | DPip | | Pap | | |
| | | | | | | DBap | | Pip | | |
| | | | | | | DMop | | Eap | | |
| | | | | | Tep | DMop | | | | |
| | | | | | | DTep | | | | |
| | | | | | Tep | DMop | | | | |
| | | | | | | DTep | | | | |
| | | DPClPhe | | | | | | | | |
| | | DPClPhe | | | | DMOp | | Pip | | |
| | | | | | | DMop | | Bap | | |
| | | | | Mop | | | | | | |
| | | | | Mop | | D3Pal | | | | |
| | | | | Arg | | DMop | | | | |
| | | | | Arg | | DPip | | | | |
| | | | | Arg | | DTep | | | | |
| | | | | | | D3Pal | | Pip | | |
| | | | | Arg | | D3Pal | | Pip | | |
| | | | | Arg | | D3Pal | | Mop | | |
| | | | | Arg | | D3Pal | | Tep | | |
| | | | | Arg | | D3Pal | | Pap | | |
| | | | | Arg | | DTep | | Pip | | |
| | | | | Arg | | DTep | | Mop | | |
| | | | DPhe | Arg | | DTep | | Tep | | |
| | | | DFPhe | Arg | | DTep | | Map | | |
| | | | DFPhe | Arg | | DTep | | Eap | | |
| | | | DFPhe | Arg | | DTep | | Pap | | |
| | | | Mep | Tep | | DPap | | Bap | | |

Upon completing the preclinical pharmacology and toxicology studies, it was possible to use these new LHRH antagonists, having high therapeutic effectiveness and low side effects, in the development of new medicines for treating endometriosis and other disorders of the reproductive endocrine system, including precocious puberty of children, prostate cancer and breast cancer. Because these LHRH antagonists suppress the secretion of gonadotropin by competing for receptors to endogenous LHRH, they can be used as a new type of contraceptive for both males and females. Moreover, the LHRH antagonists of this invention have been found to act rapidly, reversibly and safely. These new LHRH antagonists can further be used in the treatment of infertility and for selectively and reversibly abolishing the function of the pituitary gland as it relates to the secretion of gonadotropin.

Acting as a kind of medicinal peptide, the LHRH antagonists described herein are not likely to be administrated orally. However, these peptides can be easily made into a lyophilized powder which can be readily dissolved in a saline solution for injection intravenously, subcutaneously or intramuscularly.

Moreover, long-acting delivery systems, such as biodegradable, injectable capsules, have been studied. The capsules could be implanted subcutaneously by special syringe and would be absorbed by the tissue after the entire peptide content has been released. There would be no need, therefore, to remove the capsules surgically. This long-acting delivery system is especially useful for long-term, clinical administrations of the LHRH analogs.

The following analysis results for analogs IV, V, VII serve as representative examples:

(1) The Purity

Thin Layer Chromatography (TLC):

There was only a single spot on each of the chromatograms developed in the five different solvent systems.

High Performance Liquid Chromatography (HPLC):

There was only a single peak in each of the chromatograms eluted with the two different solvent systems.

Figure 2:
FIG. 2 shows the HPLC spectra for a pure sample of LHRH antagonist (V).
Conditions:
Column: μ-Bondapek C18 (3.9 mm×30 cm)
Moble Phase: A, 0.01 M KH$_2$PO$_4$ (pH 3) B, 20% A+80% acetonitrile
Gradient Procedure: B from 40% to 100% in 15 min.
Flow Rate: 2 ml/min.
Detector: UV 210 nm.
Figure 3:
FIG. 3 shows the HPLC spectra for a pure sample of LHRH antagonist (VII).
Conditions:
Column:μ-Bondapek C18 (3.9 mm×30 cm)
Moble Phase: A, 0.01 M KH$_2$PO$_4$ (pH 3) B, 20% A+80% acetonitrile
Gradient Procedure: B from 40% to 100% in 15 minutes
Flow Rate: 2 ml/min.
Detector: UV 210 nm.
Figure 4:
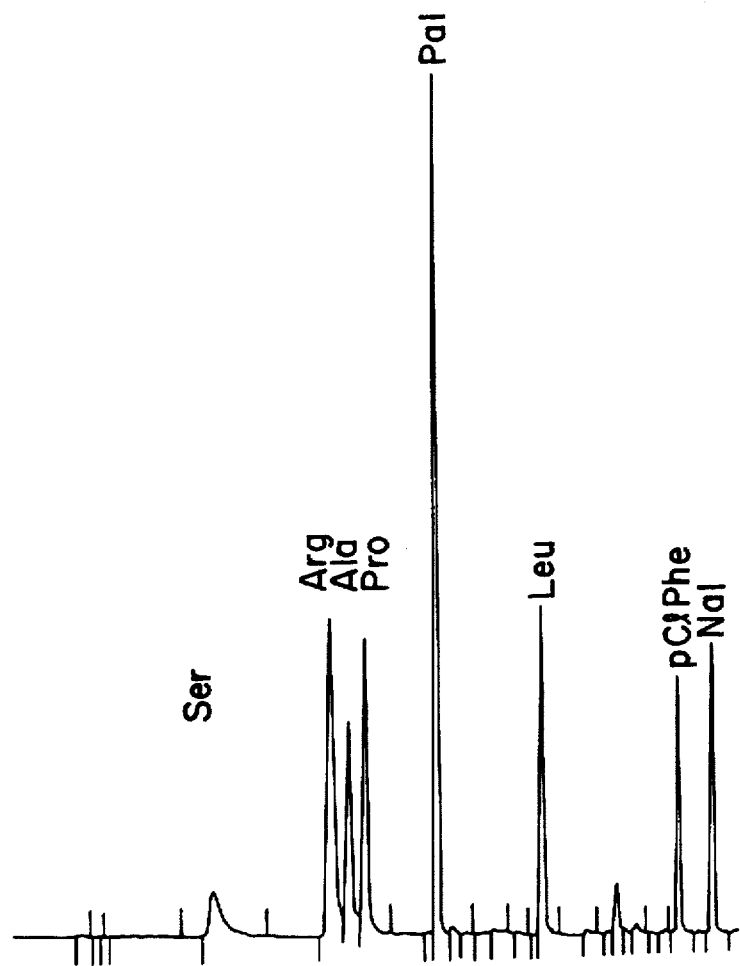
FIG. 4 shows the PICO-TAG spectra for a sample of LHRH antagonist (IV).

The rate of flow (Rf) and retention time (TR) values are shown in Table 2 and in FIGS. 1–3.

TABLE 2

The Chromatographic Analysis Results of LHRH Antagonists*

| | HPLC | | TLC | | | | |
|---|---|---|---|---|---|---|---|
| Analogs | TR1 | TR2 | Rf1 | Rf2 | Rf3 | Rf4 | Rf5 |
| IV | 7.55 | 5.26 | 0.23 | 0.21 | 0.31 | 0.19 | 0.65 |
| V | 7.90 | 8.11 | 0.32 | 0.30 | 0.35 | 0.30 | 0.69 |
| VII | 16.19 | 9.58 | 0.17 | 0.08 | 0.16 | 0.40 | 0.12 |

*All values are given in terms of minutes.

(2) Amino Acid Analysis

Figure 5:
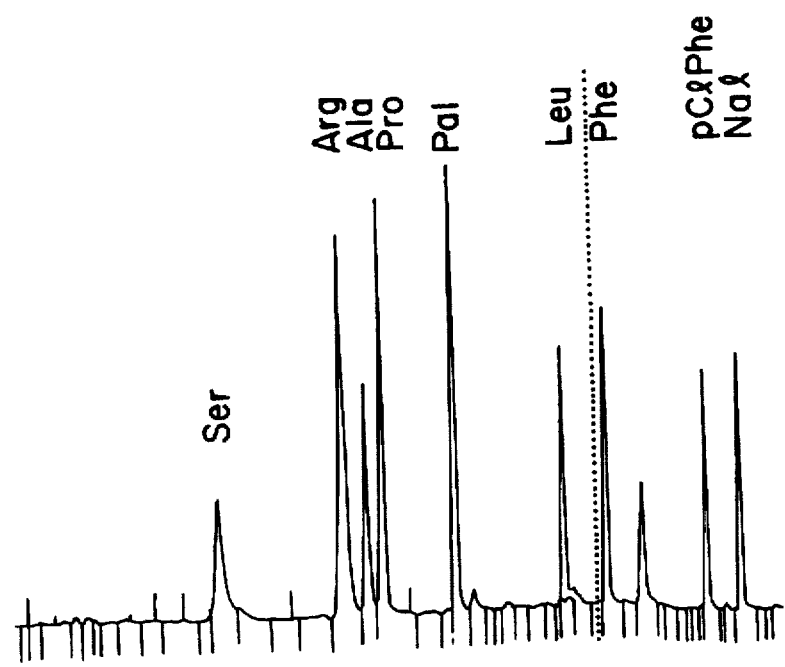
FIG. 5 shows the PICO-TAG spectra for a sample of LHRH antagonist (V).

The analyses are carried out according to the classical IEN method and the new PICO-TAG method, and the results are shown in Table 3 and FIGS. 5 and 6.

TABLE 3

The Amino Acid Composition of LHRH Antagonists

| Analogs | Methods | Ser | Arg | Ala | Pro | Leu | Phe | Pal | pClPhe | Nal |
|---|---|---|---|---|---|---|---|---|---|---|
| IV | IEN | 0.86 | 2.05 | 1.01 | 0.99 | 1.13 | | + | + | ND |
| | PICO-TAG | 0.92 | 2.25 | 0.91 | 1.01 | 0.91 | | + | + | + |
| V | IEN | 0.81 | 2.02 | 1.03 | 1.03 | 1.12 | 0.99 | + | + | + |
| | PICO-TAG | 0.68 | 2.26 | 0.93 | 1.29 | 1.04 | 1.00 | + | + | + |
| VII | IEN | 0.91 | 0.91 | 1.00 | 1.00 | 1.09 | | + | + | ND |

ND = Not Determined (3) Bioassay Results

The results of bioassay, including antiovulatory activity (AOA) at various doses and $ED_{50}$ for histamine-releasing activity (HRA) in vitro, are illustrated in Table 4 in which 26 antagonists are listed as examples.

TABLE 4

Bioassay Results of New LHRH Antagonists Based on the Parent Structure*

| | Substituted Amino Acids | % AOA/μg | | | | | HRA (μg/ml) |
|---|---|---|---|---|---|---|---|
| | | 0.125 | 0.25 | 0.5 | 1.0 | 2.0 | $ED_{50} \pm$ SEM |
| 1 | Parent* | | 50 | 75 | 100 | | 3.5 ± 0.38 |
| 2 | D-Phe$^3$ | | 29 | 60 | 100 | | 7.4 ± 0.98 |
| 3 | DPhe$^3$, DPhe | | | | 0 | | 18.5 ± 7.00 |
| 4 | DTyr$^3$, Lys$^5$ | | | | 40 | | 6.1 ± 2.15 |
| 5 | D-Phe | | | | | 60 | 35.0 ± 5.05 |
| 6 | Map$^5$ | | | 29 | | | 24.8 ± 4.47 |
| 7 | Eap$^5$ | | | 43 | | | 12.0 ± 0.50 |
| 8 | Pap$^5$ | | | 0 | | | 9.6 ± 0.19 |
| 9 | Bap$^5$ | | | 14 | | | 23.5 ± 5.78 |
| 10 | D-Map$^5$ | | | 12.5 | | | 18.3 ± 2.38 |
| 11 | Tep$^5$ | | | 14 | | | 36.8 ± 5.68 |
| 12 | Pip$^5$ | 17 | 33 | 71 | 100 | | 9.4 ± 1.63 |
| 13 | Mop$^5$ | | | 25 | 100 | | 14.7 ± 2.70 |
| 14 | D-Map$^6$ | | | 14 | | | 19.5 ± 2.50 |
| 15 | D-Map$^6$ | | | 14 | | | 13.0 ± 1.00 |
| 16 | D-Tep$^6$ | | | 71 | | | 22.5 ± 3.25 |
| 17 | D-Pip$^6$ | | | 0 | 50 | 57 | 7.6 ± 2.48 |
| 18 | D-Mop$^6$ | | | 67 | 100 | | >11 |
| 19 | Map$^8$ | | | 57 | 100 | | 5.4 ± 1.22 |
| 20 | Eap$^8$ | | | | 29 | | 56.9 ± 15.1 |
| 21 | Pap$^8$ | | | | 50 | 88 | 70.4 ± 26.8 |
| 22 | Bap$^8$ | | | | 0 | | >235 |
| 23 | Tep$^8$ | | | 25 | 100 | | 6.6 ± 2.13 |
| 24 | Pip$^8$ | | | | 43 | | 27.5 ± 2.50 |
| 25 | Mop$^8$ | | | | 71 | | 52.5 ± 17.5 |
| 26 | D-Map$^8$ | | | | 0 | | 28.0 ± 9.00 |

*The parent structure is: [NAc-D2Nal$^1$, DpClPhe$^2$, D3Pal$^3$, Ser$^4$, Arg$^5$, D3Pal$^6$, Leu$^7$, Arg$^8$, Pro$^9$, DAla$^{10}$]NH$^2$ As illustrated and described above, the LHRH antagonists designed and synthesized according to this invention show very good properties. They are pure in either TLC or HPLC analysis. Their compositions are consistent with their design. Their antifertility activity is high in that they can inhibit rat ovulation when injected subcutaneously at dosages of 0.1 to 2.0 μg at the noon of proestrus. Their histamine-related side effects are low, with the $ED_{50}$ for in vitro histamine-releasing activity being in the range of 5–300 μg/ml. And the lesions induced by the LHRH antagonists in a cutaneous anaphylactoid test in rats were as small as clinically required. The water-solubility of these peptides is very good, and all bioassays were carried out in a saline solution, so that it would be easy to formulate injections for clinical use. The peptides can also be readily used in long-acting delivery systems, among which injectable microcapsules are the most convenient for long-term suppression of gonadotropin and gonadal hormone. Therefore, these LHRH antagonists can be used as highly effective, reversible and safe contraceptives for both males and females. They can be also utilized for the treatment of various diseases related to disorders of the reproductive endocrine system, such as hormone-dependent prostate cancer and breast cancer, endometriosis and precocious puberty of children. The peptides are also useful in the treatment of infertility. The new LHRH antagonists discussed herein can be further utilized in basic research of reproductive physiology and pharmacology, such as studying the function of the pituitary gland and its affect on gonadal hormones or gonadotropins, or the affect of LHRH on sexual behavior.

ABBREVIATIONS

The following are abbreviations which have been used in the text of this patent application document.
Ala alanine
AOA antiovulatory activity
Arg arginine
Bap dibutylaminomethyl phenylalanine
Boc t-butyloxylcarbonyl
BuOAc butyl acetate
CAT cutaneous anaphylactoid test
DCC dicyclohexylcarbodiimide
DCM dichloromethane
D2Nal D-μ-(2-naphthyl) alanine
D3Pal D-μ-(3-pyridyl) alanine
DpClPhe p-chloro-D-phenyialanine
DpFPhe p-fluoro-D-phenylalanine
D6Qal D-μ-(6-quinolyl) alanine
DMF N,N-dimethyl formamide
Eap diethylaminomethyl phenylalanine
$ED_{50}$ effective dose for 50% response
EtOAC ethyl acetate
FSH follicle-stimulating hormone
Glu glutamic acid
Gly glycine
His histidine
HOBT 1-hydroxybenzotriazole
HPLC high performance liquid chromatography ninhydrin derivation
HRA histamine-releasing activity
HRT histamine-releasing test
IEN ion exchange chromatography with post-column
IPA isopropyl alcohol
LH luteinizing hormone
LHRH luteinizing hormone releasing hormone
Leu leucine
Lys lysine Map dimethylaminomethyl phenylalanine
Met methionine
Mop morpholinomethyl phenylalanine
nBuOH n-butyl alcohol
NS normal saline
Pap dipropylaminomethyl phenylalanine
Phe phenylalanine
Pip piperidinomethyl phenylalanine
PIPES Piperazine-N,N'-bis[2-ethanesulfonic acid]
Pro proline
Rf rate of flow
SE standard error
Ser serine
TFA trifluoroacetic acid
TLC thin-layer chromatography
TR retention time
Trp tryptophan
Tyr tyrosine
Tep tetrahydroperrolyl methyl phenylalanine

What is claimed is:

1. A peptide having the sequence NAc-D2Nal$^1$-AA$^2$-AA$^3$-Ser$^4$-AA$^5$-D3Pal$^6$-Leu$^7$-AA$^8$-Pro$^9$-DAla$^{10}$-NH$_2$, wherein AA$^5$ is Mop$^5$ or Arg$^5$, provided that when AA$^5$=Mop$^5$, then AA$^2$=DpClPhe$^2$, AA$^3$=D3Pal$^3$, and AA$^8$=Arg$^8$; and when AA$^5$=Arg$^5$ and AA$^3$=DPhe$^3$ then AA$^2$=DpClPhe$^2$, and AA$^8$=Arg$^8$; and when AA$^5$=Arg$^5$ and AA$^3$=D3Pal$^3$, then AA$^2$=DpClPhe$^2$ and AA$^8$=Pap$^8$.

2. A method of controlling the production of gonadotropins in a mammal, comprising the steps of administering to a mammal one or more peptides according to claim 1 in an amount effective to control the production of gonadotropins.

3. A method of preventing conception in a mammal, comprising the steps of administering to a mammal one or more peptides according to claim 1 in an amount effective to prevent conception.

4. A method of treating mammalian diseases related to disorders of the reproductive endocrine system, comprising the steps of administering to a mammal having one of said diseases one or more peptides according to claim 1 in an amount effective to treat a disease related to a disorder of the reproductive endocrine system, wherein antiovulatory activity of said peptide(s) occurs at lower concentrations than histamine releasing activity.

5. The method according to claim 4, wherein said mammalian disease is selected from the group consisting of endometriosis, precocious puberty, prostate cancer and breast cancer.

6. The method according to any one of claims 2, 3, 4 or 5, wherein at least one of the peptides is NAc-D2Nal$^1$-DpClPhe$^2$-D3Pal$^3$-Ser$^4$-Mop$^5$-D3Pal$^6$-Leu$^7$-Arg$^8$-Pro$^9$-DAla$^{10}$-NH$_2$.

7. The method according to any one of claims 2, 3, 4 or 5, wherein at least one of the peptides is NAc-D2Nal$^1$-DpClPhe$^2$-DPhe$^3$-Ser$^4$-Arg$^5$-D3Pal$^6$-Leu$^7$-Arg$^8$-Pro$^9$-DAla$^{10}$-NH$_2$.

8. The method according to any one of claims 2, 3, 4 or 5, wherein at least one of the peptides is NAc-D2Nal$^1$-DpClPhe$^2$-DPhe$^3$-Ser$^4$-Tyr$^5$-D3Pal$^6$-Leu$^7$-Arg$^8$-Pro$^9$-DAla$^{10}$-NH$_2$.

* * * * *